United States Patent [19]

Shutske et al.

[11] Patent Number: 5,686,483

[45] Date of Patent: Nov. 11, 1997

[54] AMINOALKYLOXIMES

[75] Inventors: Gregory M. Shutske, Pittstown; Brian S. Freed, Phillipsburg, both of N.J.; John D. Tomer, IV, Perkasie, Pa.; R. Richard L. Hamer, Lebanon, N.J.

[73] Assignee: Hoechst Marion Roussel, Inc., Cincinnati, Ohio

[21] Appl. No.: 457,422

[22] Filed: Jun. 1, 1995

Related U.S. Application Data

[62] Division of Ser. No. 285,668, Aug. 3, 1994.

[51] Int. Cl.$^6$ ............ C07D 295/13; C07D 207/08; C07D 403/04; C07D 403/12

[52] U.S. Cl. ............ 514/428; 546/232; 546/199; 546/208; 546/210; 546/229; 546/221; 548/518; 548/569; 548/336.1; 548/312.4; 548/313.7; 548/314.7; 548/539; 548/341.5; 544/59; 544/162; 544/139; 544/141; 544/62; 544/60; 544/56; 544/122; 544/130; 544/187; 544/189; 540/610; 540/596; 540/544; 540/480; 540/467; 540/450; 540/603; 540/602; 540/483; 540/609; 540/482; 540/604; 540/481; 540/598; 514/227.5; 514/238.2; 514/212; 514/211; 514/183; 514/422; 514/322; 514/233.8; 514/331; 514/237.2; 514/228.2; 514/227.8; 564/256

[58] Field of Search ............ 548/569; 514/428, 514/331, 227.8, 212, 211; 546/208; 544/60; 540/602, 544

[56] References Cited

U.S. PATENT DOCUMENTS

| | | | |
|---|---|---|---|
| 3,636,111 | 1/1972 | Karten | 260/566 |
| 4,085,225 | 4/1978 | Welle et al. | 424/304 |
| 4,239,901 | 12/1980 | Rainer | 560/34 |
| 4,297,359 | 10/1981 | van Zorge | 424/263 |
| 4,328,227 | 5/1982 | Ulrich et al. | 424/250 |
| 4,352,804 | 10/1982 | van Zorge | 424/250 |
| 4,459,410 | 7/1984 | Ono et al. | 546/236 |
| 4,465,678 | 8/1984 | Knops et al. | 424/244 |
| 4,851,423 | 7/1989 | Girijavaliabhan et al. | 514/399 |
| 5,064,824 | 11/1991 | Acton et al. | 514/202 |
| 5,126,444 | 6/1992 | Acton et al. | 540/215 |

FOREIGN PATENT DOCUMENTS

| | | |
|---|---|---|
| 0053107 | 6/1982 | European Pat. Off. |
| 9113062 | 9/1991 | WIPO |

OTHER PUBLICATIONS

T. Sakamoto, et al., Chemical and Pharmaceutical Bulletin, 34, 2754 (1986) published in Japan and entitled "Heteroaromatic Ring Systems, VIII. Synthesis of 3–Substituted Isocoumarins from O–Halobenzoic Acid Derivatives". month of publication not provided.

A. N. Tischler and T. J. Lanza, Tetrahedron Letters, 27, 1653 (1986) published in Great Britain and entitled "6–Substituted Indoles from O–Halonitrobenzenes". month of publication not provided.

*Primary Examiner*—Mukund J. Shah
*Assistant Examiner*—King Lit Wong
*Attorney, Agent, or Firm*—Raymond R. Wittekind; Kenneth A. Genoni; Edlyn S. Simmons

[57] ABSTRACT

Novel aminoalkyloximes, precursors and processes for the preparation thereof, and methods of treating depression and obsessive compulsive disorders are described.

5 Claims, No Drawings

AMINOALKYLOXIMES

This is a division of prior application Ser. No. 08/285,668 filed Aug. 3, 1994.

The present invention relates to aminoalkyloximes. More particularly, the present invention relates to aminoalkyloximes of formula 1

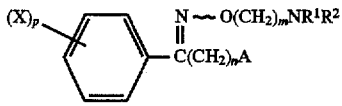

wherein:

a. X is hydrogen, loweralkyl, loweralkoxy, halogen, trifluoromethyl, or a group of the formula

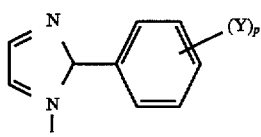

wherein Y is hydrogen or loweralkyl, and p is 1 or 2;

b. A is a group of the formula

a group of the formula

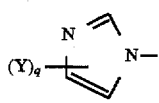

wherein Y is as above and q is 1 or 2; a group of the formula

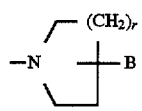

wherein B is a group of the formula

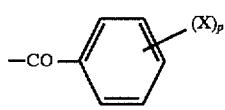

wherein X and p are as above or a group of the formula

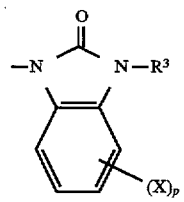

wherein $R^3$ is hydrogen or loweralkyl and X and p are as above and r is 1, 2, or 3;

c. $R^1$ and $R^2$ are independently hydrogen or loweralkyl or $R^1$ and $R^2$ taken together with the nitrogen atom to which they are attached form a group of the formula

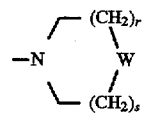

wherein W is $CH_2$, O, or S, r is as above; and s is 1, 2, or 3;

d. m is 2 to 6, inclusive, and n is 0, or 2 to 6, inclusive, the geometric and optical isomers thereof; or the pharmaceutically acceptable salts thereof, which are useful for treating depression and obsessive compulsive disorders, alone or in combination with adjuvants.

Subgeneric thereto are aminoalkyoximes wherein:

a. A is a group of the formula

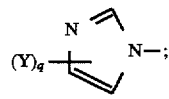

b. A is a group of the formula

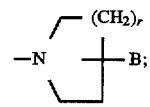

and c. A is a group of the formula

and X is

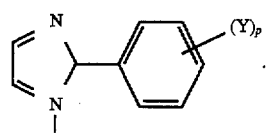

Also included in the present invention are compounds of the formula

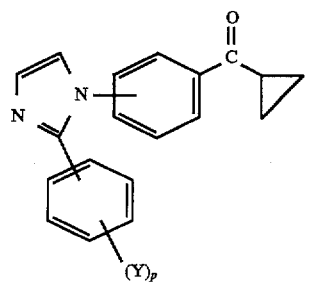

wherein Y is hydrogen or loweralkyl and p is 1 or 2.

As used throughout the specification and appended claims, the term "alkyl" refers to a straight or branched chain hydrocarbon radical containing no unsaturation and having 1 to 8 carbon atoms. Examples of alkyl groups are methyl, ethyl, 1-propyl, 2-propyl, 1-butyl, 1-hexyl, 3-hexyl, 4-heptyl, 2-octyl and the like. The term "alkoxy" refers to a monovalent substituent which consists of an alkyl group linked through an ether oxygen having its free valence bond from the ether oxygen. Examples of alkoxy groups are methoxy, ethoxy, propoxy, 1-butoxy, 1-pentoxy, 3-hexoxy, 4-heptoxy, 2-octoxy and the like. The term "alkanol" refers to a compound formed by a combination of an alkyl group and hydroxy radical. Examples of alkanols are methanol, ethanol, 1- and 2-propanol, 2,2-dimethylethanol, hexanol, octanol and the like. The term "halogen" refers to a member of the family fluorine, chlorine, bromine, or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by synthesis from optically active precursors.

The aminoalkyloximes of formula 1 exist in isomeric Z- and E-forms. For example, 3-(1H-imidazolyl) propiophenone-O-(2-aminoethyl)oxime exists in the Z- and E-isomeric forms, 2 and 3, respectively, as shown below:

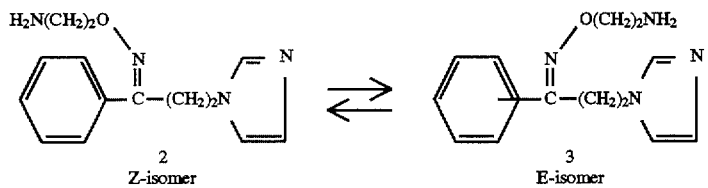

In the Z-isomer, the aminoalkyloxy group of the oxime function and the phenyl moiety, the group of greater priority, are cis to each other and in the E-isomer, the aminoalkyloxy group of the oxime function and the phenyl moiety, are trans to each other. The wiggly (~) line in the formulas of the aminoalkyloximes of formula I indicate that the compound may be the E- or Z-isomer. See B. Unterhalt, Methodicum Chimicum 6, 403 (1975), for a discussion of the E-Z nomenclature.

The present invention comprehends all optical isomers and racemic forms thereof of the compounds disclosed and claimed herein and the formulas of the compounds shown herein are intended to encompass all possible optical isomers of the compounds so depicted.

The novel aminoalkyloximes 1 are prepared by condensing a phenone 4 with an aminooxyalkylamine 5 as illustrated below:

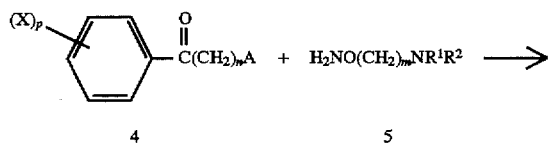

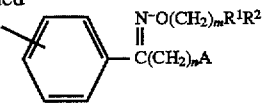

wherein A, $R^1$, $R^2$, X, m, n, and p are as hereinbefore-described. The condensation is generally performed by treating a phenone 4 with an aminooxyalkylamine 5 as a salt, for example, a dihydrohalide 5a

wherein Hal is chloro or bromo, chloro being preferred, in the presence of an acid acceptor, for example, a tertiary amine such as a trialkylamine (trimethylamine, triethylamine, tripropylamine, and the like) or a heteroaromatic amine (pyridine, picoline, lutidine, s-collidine, and the like), a heteroaromatic amine, namely, pyridine being preferred. While the condensation proceeds readily in the tertiary amine, for example, pyridine, acting as both an acid acceptor and solvent, a cosolvent, for example, an alkanol such as ethanol may be used to facilitate the reaction. The condensation temperature is not narrowly critical, the condensation is preferably performed at the reflux temperature of the reaction medium.

The requisite phenones 4 and aminooxyalkylamines 5 are prepared by the processes shown in the Reaction Scheme. To prepare a phenone 4, for example, a benzene 6 is treated with a carbonylhalide 7 having a leaving group L, i.e., a halo group such as chloro or bromo, or a sulfonyloxy group such as methylsulfonyloxy, phenylsulfonyloxy, or 4-methylphenylsulfonyloxy in the presence of a Friedel-Crafts catalyst such as aluminum chloride to afford an intermediate phenone 8, which is then treated with a nucleophile AH 9 in the presence of a base, e.g., a tertiary amine (triethylamine or pyridine) or an alkali metal carbonate or -bicarbonate (sodium carbonate or potassium bicarbonate) to yield the ultimate phenone 4 by well-known methods.

Alternatively, a phenone 4 is prepared by condensing an alkyne 10 having a leaving group L wherein L is as described above with a nucleophile AH 9 in an aprotic dipolar solvent such as dimethylformamide at a temperature of about 60° to 80° C. to provide a substituted alkyne 11, which is sequentially treated with a halobenzene of the formula 12

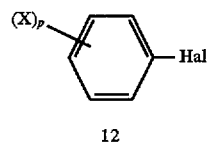

wherein X, p, and Hal are as described above in a condensation medium of bis(triphenylphosphine) palladium (II)

chloride, copper (I) iodide, and triethylamine, and then a hydration medium of sulfuric acid in the presence of mercury (II) sulfate in aqueous ethanol to provide phenylalkyne 13 and ultimate phenone 4, respectively. See T. Sakamuto, et al., Chemical and Pharmaceutical Bulletin (Japan) 34, 2754 (1986) and A. N. Tischler and T. J. Lanza, Tetrahedron Letters, 27, 1653 (1986). The aminooxyalkylamines 5 are prepared by treating N-hydroxyphthalimide 14 with an N-substituted phthalimide 15 having a leaving group L wherein L is as described above in the presence of an alkali metal carbonate, e.g., potassium carbonate, in an aprotic dipolar solvent, e.g., dimethylformamide, to form coupled product 16, cleaving the coupled product 16 with hydrazine in an alkanol, e.g., ethanol, to provide an aminoalkylhydroxyamine 17, and then alkylating an aminoalkylhydroxylamine 17 with an alkyl halide or -dihalide of the formula 18, 19, or 20

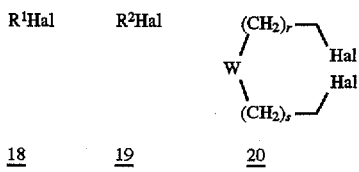

$R^1$Hal  $R^2$Hal 18        19        20 in the presence of a trialkylamine, e.g., triethylamine to yield 5. See Organic Chemistry, D. J. Cram and G. S. Hammond, McGraw-Hill, New York, N.Y., 1959, page 215.

The aminoalkyloximes of the present invention are useful as agents for the alleviation of depression and affective disorders such as obsessive compulsive disorders, particularly those associated with serotonergic hypofunction. See, for example, W. K. Goodman, et al., Archives of General Psychiatry, 47, 577 (1990). Alleviation of depression and affective disorders, including obsessive compulsive disorders, is demonstrated in the in vitro inhibition of serotonin uptake, an assay for the determination of the ability of a drug to inhibit the reuptake of serotonin, a neurotransmitter implicated in the etiology of depression and affective disorders. In this assay, a modification of the tests described by A. S. Horn and R. C. A. M. Trace, British Journal of Pharmacology, 51, 399 (1974), A. Nagy and A. V. Delgado-Escueta, Journal of Neurochemistry, 43, 1114 (1984) and P. R. Dunkley, et al., Brain Research, 372, 115 (1986), the following reagents are prepared and employed:

Procedure

A. Animals

Male CR Wistar rats (100–125 g)

B. Reagents

1. Krebs-Henseleit Bicarbonate Buffer, pH 7.4 (KHBB): Prepare a 1 liter batch, containing the following salts.

|  | grams/L | mM |
| --- | --- | --- |
| NaCl | 6.92 | 118.4 |
| KCl | 0.35 | 4.7 |
| MgSO$_4$.7H$_2$O | 0.29 | 1.2 |
| KH$_2$PO$_4$ | 0.16 | 2.2 |
| NaHCO$_3$ | 2.10 | 24.9 |
| CaCl$_2$ | 0.14 | 1.3 |
| Prior to use add to 200 ml, per assay: | | |
| Dextrose | 2 mg/ml | 11.1 |
| Iproniazid phosphate | 0.30 mg/ml | 0.1 |

The batch is aerated for 60 minutes with 95% oxygen/5% carbon dioxide, the pH is checked to insure it is at 7.4±0.1, then add bovine serum albumin (Sigma cat# A-7906) 1 mg/ml.

2. Filtration buffer:
Make a 4 liter batch containing the following salts:

|  | grams/4L | mM |
| --- | --- | --- |
| NaCl | 31.68 | 135.5 |
| KCl | 1.40 | 4.7 |
| MgSO$_4$.7H$_2$O | 1.16 | 1.2 |
| HEPES | 9.54 | 10.0 |
| CaCl$_2$ | 0.56 | 1.3 |
| BSA | 4.0 | 1 mg/ml |

Maintain on ice.

3. Sucrose solution: 0.32M sucrose containing 5 mM HEPES and 0.1 mM EDTA; pH to 7.3 using Tris base.

4. A 0.1 mM stock solution of serotonin creatinine SO$_4$ is made up in 0.01N HCl. This is used to dilute the specific activity of radiolabeled 5HT.

5. 5-[1,2-$^3$H(N)]-Hydroxytryptamine creatinine sulfate (serotonin), specific activity 20–30 Ci/mmol, is used. The final desired concentration of [$^3$H]-5HT in the assay is 50 nM. The dilution factor is 0.8. The KHBB is made up to contain 62.5 nM of [$^3$H]-5HT.

Add to 100 ml of KHBB:

| A) 56.1 μl of 0.1 mM 5HT = | 56.1 nM |
| --- | --- |
| B) 0.64 nmol of [$^3$H]-5HT = | 6.4 nM |
|  | 62.5 nM |

6. For most assays, a 0.5 mM stock solution of the test compound is made up initially in either 10 μl of glacial acetic acid, 100 μl DMSO or 10 μl of the recrystallization solvent, to which is added approximately 10 ml of distilled water. Compounds are initially screened in duplicate at 3 concentrations ($10^{-8}$, $10^{-7}$ and $10^{-6}$M) made up in water. For those compounds demonstrating activity at $\leq 10^{-7}$ in the initial screen, IC$_{50}$s are determined from 7 concentrations: $10^{-9}$ through $10^{-6}$. Higher or lower concentration ranges may be used depending on the potency of the compound. To ensure consistency, the standard chlomipramine is run with each assay.

C. Tissue Preparation

Male Wistar rats are decapitated and the brain rapidly removed. Whole brain (minus cerebellum) is weighed and homogenized in 15 volumes of ice cold sucrose solution using a Potter-Elvejhem homogenizer. The following procedures are performed on ice. Homogenization should be done with 4–5 up and down strokes at medium speeds (setting 4.5 to 5) to minimize synaptosome lysis. The homogenate is centrifuged at 1000 g (3000 rpm, Sorvall SS-34 rotor) for 10 minutes at 0°–4° C. The supernatant is removed and approximately 10 ml per tube is carefully layered onto a discontinuous Percoll (Sigma cat#P-1644) gradient: 21% Percoll in sucrose solution at the bottom (15 ml per tube) and 10% Percoll in the middle (10 ml; colored with a few drops of phenol red for visibility).

The Percoll gradient tubes are carefully placed into a Beckman SW-28 swinging bucket rotor and spun in a Beckman XL90 ultracentrifuge using the following program: speed, 11,000 rpm (15,000 g) for 30 minutes at 4° C.; slow acceleration and deceleration (acceleration setting 9; deceleration setting 3). Tubes are carefully removed, and the top layer and the top part of the middle (red) layers are discarded using a pasteur pipette. The synaptosomes are located in the white fluffy band at the interface between the 10% and 21% Percoll layers. This is carefully removed, placed in a centrifuge tube, diluted with KHBB and spun at 21,000 g (13,000 rpm, Sorvall SS-34 rotor). The pellet (synaptosomes) is resuspended in KHBB (10 vol per gram original brain wet weight; 1 brain minus cerebellum weighs approximately 1.2 g; 2.5 brains are needed per typical assay).

D. Assay

| 800 µl | KHBB with [$^3$H]-5HT |
| 20 µl | Vehicle or appropriate drug |
| 200 µl | Tissue suspension concentration |

200 µl of the tissue suspension are added to each of 24 tubes (at a time) containing the 20 µl of vehicle or drug on ice. Three minutes later, 800 µl of KHBB containing [$^3$H]-5HT are added, and tubes are vortexed. The rack containing the 24 tubes is moved from the ice bath to a water bath set at 37° C. The tubes are incubated for 5 minutes under 95% oxygen/5% carbon dioxide. Uptake is terminated by filtration through GF/B filter strips using a Brandel cell harvester (filter strips are presoaked in ice cold filtration buffer). Tubes are washed once with 5 ml of ice cold filtration buffer. Filter disks are placed in scintillation vials to which are added 10 ml of scintillation fluid (EcoScint). Filters are allowed to sit overnight before being counted.

For each assay, 3 tubes are incubated with 20 µl of vehicle at both 37° C. and 0° C. Active uptake is the difference between cpm taken up at 37° C. and 0° C. Percent inhibition at each concentration is the mean of two determinants. $IC_{50}$ values are derived from log probit analysis using #46 Litchfield and Wilcoxon I: confidence limits of $IC_{50}$ Pharmacologic Calculation System—version 4.0.

TABLE A

| Compound | Inhibition of Serotonin Reuptake Activity $IC_{50}$(µM) |
|---|---|
| 4'-Chloro-3-(1-(1H)-imidazolyl)propiophenone-O-(2-aminoethyl)oxime | 0.128 |
| 4'-Methoxy-3-(1-(1H)-imidazolyl)propiophenone-O-(2-aminoethyl)oxime | 1.28 |
| 4'-(1-(1H)-imidazolyl)-1-phenyl-1-butanone O-(2-aminoethyl)oxime | 1.81 |
| 3-(1-(1H)-imidazolyl)-1-(4-trifluoromethyl-phenyl)-1-propanone O-(2-aminoethyl)oxime | 0.164 |
| 1-(4-chlorophenyl)-4-(1-(1H)-imidazolyl)-1-butanone O-(2-aminoethyl)oxime | 0.160 |
| 1-(4-fluorophenyl)-4-(1-(1H)-imidazolyl)-1-butanone O-(2-aminoethyl)oxime | 0.257 |
| 4-(2-methyl-1-(1H-)imidazolyl-1-phenyl-1-butanone O-(1-aminoethyl)oxime | 0.656 |
| 4-(1-(1H)-imidazolyl)-1-(4-trifluoromethyl phenyl)-1-butanone O-(2-aminoethyl)oxime | 0.080 |
| Amitriptyline (standard) | 0.091 |
| Fluoxetine (standard) | 0.042 |

Alleviation of depression and affective disorders is achieved when the present aminoalkyoximes are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Compounds of the invention include:
a. 3-(1-(1H)-imidazolyl)-1-(2-methoxyphenyl)-1-propanone O-(2-aminoethyl)oxime;
b. 3-(1-(1H)-imidazolyl)-1-(2-methylphenyl)-1-propanone O-(2-aminoethyl)oxime;
c. 3-(2,4-dimethyl-(1H)-imidazolyl)propiophenone O-(2-aminoethyl)oxime;
d. 4-[4-(3-methylbenzoyl)-1-piperidinyl]-1-phenyl-1-butanone O-(2-aminoethyl)oxime;
e. 4-[4-(2,4-dimethylbenzoyl)-1-piperidinyl]-1-phenyl-1-butanone O-(2-aminoethyl)oxime;
f. 4-[4-(4-methoxybenzoyl)-1-piperidinyl]-1-phenyl-1-butanone O-(2-aminoethyl)oxime;
g. 4-[4-(4-trifluoromethylbenzoyl)-1-piperidinyl]-1-phenyl-1-butanone O-(2-aminoethyl)oxime;
h. 4-[4-(benzoyl)-1-piperidinyl]-1-phenyl-1-butanone O-(2-aminoethyl)oxime;
i. 4-[3-(4-fluorobenzoyl)-1-pyrrolidinyl]-1-phenyl-1-butanone O-(2-aminobutyl)oxime;
j. 4-[4-(4-fluorobenzoyl)-1-hexahydroazepinyl]-1-phenyl-1-butanone O-(2-aminoethyl)oxime;
k. 1-{1-[4-(2-aminoethoxyimino)-4-(4-chlorophenyl)butyl]-4-piperidinyl}-1,3-dihydro-3-methyl-2-benzimidazolone;
l. 3-(1-(1H)-imidazolyl)-1-(4-trifluoromethylphenyl)-1-propanone O-[2-(1-piperidinyl)ethyl]oxime;
m. 3-(1-(1H)-imidazolyl)-1-(4-trifluoromethylphenyl)-1-propanone O-[2-(1-pyrrolidinyl)ethyl]oxime;
n. 3-(1-(1H)-imidazolyl)-1-(4-trifluoromethylphenyl)-1-propanone O-[2-(1-hexahydroazepinyl)ethyl]oxime;
o. 3-(1-(1H)-imidazolyl)-1-(4-trifluoromethylphenyl)-1-propanone O-[2-(1-morpholinyl)ethyl]oxime; and
p. 3-(1-(1H)-imidazolyl)-1-(4-trifluoromethylphenyl)-1-propanone O-[2-(1-thiomorpholinyl)ethyl]oxime.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl, salicylate, or orange flavoring may be added. When the dosage unit is a capsule, it may contain, in addition to materials of the above type, a liquid carrier such as fatty oil. Either dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following examples are for illustrative purposes only and are not to be construed as limiting the invention.

EXAMPLE 1

3-(1-(1H)-Imidazolyl)propiophenone-O-(2-aminoethyl)oxime Difumarate

A mixture of 3-((1H)-imidazolyl)propiophenone (2.74 g), 2-aminooxyethylamine dihydrochloride (2.65 g), and pyridine (100 mL) was heated under reflux, under nitrogen, for two hrs. The reaction mixture was concentrated, and the residue was pumped under high vacuum and then flash chromatographed (1:1:18 triethylamine methanol/dichloromethane, then 1:1:8 triethylamine/methanol/dichloromethane). The appropriate fractions were collected and concentrated. The residue was distributed between 10% sodium hydroxide solution and ethyl acetate. The layers were separated, and the organic layers were dried over anhydrous magnesium sulfate, filtered, and the filtrate was concentrated and pumped under high vacuum, at steam bath temperature. To the residue in methanol was added fumaric acid (2.04 g), then ethyl acetate, carefully, to precipitate the salt. The solid was collected and dried under high vacuum at 56° C. The solid was slurried in a small amount of methanol to yield 1.02 g (15.2%) of product, mp 130.5°–132° C., after drying under high vacuum for four hrs at 97° C.

Analysis: Calculated for $C_{14}H_{18}N_4O \cdot C_8H_8O_8$: 53.88% C 5.34% H 11.42% N Found: 53.44% C 5.30% H 11.36% N

EXAMPLE 2

3-(1-(1H)-Imidazolyl)-1-(4-trifluoromethylphenyl)-1-propanone O-(2-Aminoethyl)oxime Dihydrochloride A mixture of 3-(1-(1H)-imidazolyl)-1-(4-trifluoromethylphenyl)-1-propanone (4.65 g), O-(2-aminoethyl)hydroxylamine dihydrochloride (3.10 g), 3 equivalents of pyridine, and absolute ethanol (75 ml) was heated under reflux, under nitrogen, with stirring, for two hrs. The reaction mixture was diluted with 10% sodium hydroxide solution and ethyl acetate. The layers were separated. The aqueous phase was extracted with ethyl acetate, the organic layers were dried over anhydrous sodium sulfate, filtered, and the filtrate was evaporated. The residue was taken up in toluene and evaporated. The residue was flash it chromatographed (180:19:1 dichloromethane/methanol/ammonium hydroxide). The appropriate fractions were collected and concentrated. The residue was dissolved in absolute ethanol and treated with ethereal hydrogen chloride. Diethyl ether was added to the solution. The solid was collected and recrystallized twice from absolute ethanol/ether to give 2.8 g (40%) of product, mp 213°–214° C. (dec).

Analysis: Calculated for $C_{15}H_{19}Cl_2F_3N_4O$: 45.13% C 4.80% H 14.03% N Found: 44.82% C 4.69% H 13.98% N

EXAMPLE 3

3-(1-(1H)-Imidazolyl)-1-(3-trifluoromethylphenyl)-1-propanone O-(2-Aminoethyl)oxime Dihydrochloride A mixture of 3-(1-(1H)-imidazolyl)-1-(3-trifluoromethylphenyl)-1-propanone (4.60 g), O-(2-aminoethyl)hydroxylamine dihydrochloride (3.07 g), 3 equivalents of pyridine, and absolute ethanol (75 ml) was stirred under reflux, under nitrogen, for three hrs. The reaction mixture was diluted with 10% sodium hydroxide solution and ethyl acetate. The layers were separated. The aqueous phase was extracted with ethyl acetate, the organic layers were dried over anhydrous sodium sulfate, filtered, and the filtrate was evaporated. The residue was taken up in toluene and evaporated. The residue was flash chromatographed (180:19:1 dichloromethane/methanol/ammonium hydroxide). The appropriate fractions were collected and concentrated. The residue was dissolved in absolute ethanol and treated with ethereal hydrogen chloride. Diethyl ether was added to the solution. The solid was collected and recrystallized twice from absolute ethanol/ether to give 2.2 g (32%) of product, mp 223°–225° C. (dec.)

Analysis: Calculated for $C_{15}H_{19}Cl_2F_3N_4O$: 45.13% C 4.80% H 14.03% N Found: 45.19% C 4.69% H 13.99% N

EXAMPLE 4

4'-Methoxy-3-(1-(1H)-imidazolyl)propiophenone O-(2-Aminoethyl)oxime Difumarate Hydrate A mixture of 4'-methoxy-3-(1-(1H)-imidazolyl) propiophenone (1.47 g), 2-aminooxyethylamine dihydrochloride (1.14 g), ethanol (50 mL), and pyridine (1.55 mL) was heated under reflux, under nitrogen, for six hrs. The reaction mixture was concentrated, pumped under high vacuum, and the residue was flash chromatographed (1:1:8 triethylamine/methanol/dichloromethane). The appropriate fractions were collected and concentrated, and the residue was pumped under high vacuum at 100° C. The residue was distributed between 10% sodium hydroxide solution and ethyl acetate. The organic layers were dried over anhydrous magnesium sulfate, filtered, and the filtrate was concentrated. To the residue in methanol was added fumaric acid (1.26 g), then ethyl acetate, carefully, to precipitate the salt. The precipitate was collected under nitrogen and dried under high vacuum at 56° C. for five hrs. The residue was triturated with pentane and dried under high vacuum at 56° C. to give 1.06 g (30.8%) of product, mp 88°–90° C.

Analysis: Calculated for $C_{15}H_{20}N_4O_2 \cdot C_8H_8O_8 \cdot H_2O$: 51.30% C 5.62% H 10.40% N Found: 51.01% C 5.51% H 10.29% N

EXAMPLE 5

4'-Methoxy-3-(2-methyl-1-(1H)-imidazolyl) propiophenone O-(2-Aminoethyl)oxime Difumarate A mixture of 4'-methoxy-3-(2-methyl-1-(1H)-imidazolyl) propiophenone (1.67 g), 2-aminooxyethylamine dihydrochloride (1.23 g), ethanol (60 mL), and pyridine (2.0 mL), was heated under reflux, under nitrogen, for two hrs. The reaction mixture was concentrated, pumped under high vacuum, and flash chromatographed (1:1:8 triethylamine/methanol/dichloromethane). The appropriate fractions were collected and concentrated. The residue was distributed between 10% sodium hydroxide solution and ethyl acetate. The layers were separated and the organic layers were dried over anhydrous magnesium sulfate, filtered, and the filtrate was concentrated and pumped under high vacuum at 100° C. To the residue in methanol was added fumaric acid (1.29 g), then ethyl acetate, carefully, to precipitate the salt. The precipitate was recrystallized from methanol and ethyl acetate and dried under high vacuum at 97° C. to yield 2.08 g (56.7%) of product, mp 168°–169° C.

Analysis: Calculated for $C_{16}H_{22}N_4O_2 \cdot C_8H_8O_8$: 53.93% C 5.66% H 10.48% N Found: 53.97% C 5.57% H 10.27% N

EXAMPLE 6

4'-Chloro-3-(1-(1H)-imidazolyl)propiophenone O-(2-Aminoethyl)oxime Difumarate

A mixture of 4'-chloro-3-(1-(1H)-imidazolyl) propiophenone (1.7 g), 2-aminooxyethylamine dihydrochloride (1.4 g), and pyridine (50 mL), was heated under reflux, under nitrogen, for four hrs. The reaction mixture was concentrated, pumped under high vacuum, and the residue was flash chromatographed (1:1:18 triethylamine/methanol/dichloromethane). The appropriate fractions were collected and concentrated. The residue was distributed between 10% sodium hydroxide solution and ethyl acetate. The layers were separated and the organic layers were dried over anhydrous magnesium sulfate, filtered and the filtrate was concentrated, and pumped under high vacuum, at 100° C. for one hr. To the residue in methanol was added fumaric acid (1.29 g), then ethyl acetate, carefully, to precipitate the salt. The precipitate was dried under high vacuum at 97° C. to yield 2.23 g (58.8%) of product, mp 153°–153.5° C.

Analysis: Calculated for $C_{14}H_{17}N_4OCl \cdot C_8H_8O_8$: 50.34% C 4.80% H 10.67% N Found: 50.29% C 4.89% H 10.49% N

EXAMPLE 7

4'-Chloro-3-(2-methyl-1-(1H)-imidazolyl) propiophenone O-(2-Aminoethyl)oxime Sesquifumarate A mixture of 4'-chloro-3-(2-methyl-1-(1H)-imidazolyl) propiophenone (3.56 g), 2-aminooxyethylamine dihydrochloride (2.77 g), and pyridine (150 mL) was heated under reflux, under nitrogen, for two hrs. The reaction was concentrated, pumped under high vacuum, and flash chromatographed (1:1:18 triethylamine/methanol/dichloromethane, then 1:1:8 triethylamine/methanol/dichloromethane). The appropriate fractions were collected and concentrated. The residue was distributed between 10% sodium hydroxide solution and ethyl acetate. The layers were separated and the organic layers were dried over anhydrous magnesium sulfate, filtered, and the filtrate was concentrated and pumped under high vacuum. To the residue in methanol was added fumaric acid (1.7 g), then ethyl acetate, carefully, to precipitate the salt. The precipitate was collected and recrystallized from methanol and ethyl acetate and dried under high vacuum at 111° C. to yield 2.97 g (43.2%) of product, mp 179°–180° C.

Analysis: Calculated for $C_{15}H_{19}N_4OCl \cdot C_6H_6O_6$: 52.45% C 5.24% H 11.65% N Found: 52.05% C 5.27% H 11.30% N

EXAMPLE 8

3-(2-Methyl-1-(1H)-imidazolyl)propiophenone O-(2-Aminoethyl)oxime Difumarate

A mixture of 3-(2-methyl-1-(1H)-imidazolyl) propiophenone (4.0 g), 2-aminooxyethylamine dihydrochloride (3.34 g), and pyridine (200 mL) was heated under reflux, under nitrogen, for one hr. Additional amine (175 mg) was added, and the mixture was heated for one-half hr. The reaction mixture was concentrated, pumped under high vacuum, and the residue was flash chromatographed (1:1:18 triethylamine/methanol/dichloromethane, then 1:1:8 triethylamine/methanol/dichloromethane). The appropriate fractions were collected and concentrated. The residue was distributed between 10% sodium hydroxide solution and ethyl acetate. The layers were separated and the organic layers were dried over anhydrous sodium sulfate, filtered, and the filtrate was concentrated and pumped under high vacuum. To the residue in methanol was added fumaric acid (1.68 g), then ethyl acetate, carefully, to precipitate the salt. The precipitate was dried under high vacuum at 78° C. to yield 2.63 g (28.1%) of product, mp 138° C.

Analysis: Calculated for $C_{15}H_{20}N_4O \cdot C_8H_8O_8$: 54.76% C 5.59% H 11.11% N Found: 54.67% C 5.57% H 10.91% N

EXAMPLE 9

1-(4-Fluorophenyl)-3-(1-(1H)-imidazolyl)-1-propanone O-(2-Aminoethyl)oxime Dihydrochloride A mixture of 1-(4-fluorophenyl)-3-(1-(1H)-imidazolyl)-1-propanone (3.00 g), O-(2-aminoethyl)hydroxylamine dihydrochloride (2.46 g), 3 equivalents of pyridine and absolute ethanol (75 ml) was heated under reflux, under nitrogen, with stirring, for two hrs. The reaction mixture was partitioned between 20% sodium hydroxide solution and ethyl acetate. The layers were separated, and the aqueous phase was extracted with ethyl acetate. The combined organic extracts were dried over anhydrous sodium sulfate, filtered, and the filtrate was evaporated. The residue was taken up in toluene and evaporated. The residue was purified by flash chromatography (180:19:1 dichloromethane/methanol/ammonium hydroxide). The appropriate fractions were collected and concentrated. The residue was dissolved in absolute ethanol and treated with ethereal hydrogen chloride. Diethyl ether was added. The precipitate was collected and recrystallized twice from absolute ethanol/ether to give 1.9 g (40%) of product, mp 225°–226° C. (dec).

Analysis: Calculated for $C_{14}H_{19}Cl_2FN_4O$: 48.15% C 5.48% H 16.04% N Found: 48.34% C 5.54% H 16.04% N

EXAMPLE 10

4-(1-(1H)-Imidazolyl)-1-phenyl-1-butanone O-(2-Aminoethyl)oxime Dihydrochloride A mixture of 4-(1-(1H)-imidazolyl)-1-phenyl-1-butanone (3.00 g), O-(2-aminoethyl)hydroxylamine dihydrochloride (2.50 g), 3 equivalents of pyridine, and absolute ethanol (75 ml) was heated under reflux, under nitrogen, with stirring, overnight. The reaction mixture was evaporated, toluene was added and evaporated. The residue was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was combined with 5.0 g of crude, previously prepared material and purified by flash chromatography (180:19:1 dichloromethane/methanol/ammonium hydroxide). The appropriate fractions were collected and concentrated. The residue was dissolved in absolute ethanol and treated with ethereal hydrogen chloride. Diethyl ether was added. The precipitate was collected and recrystallized from absolute ethanol to give 6.3 g (58%) of product, mp 196°–198° C. (dec).

Analysis: Calculated for $C_{15}H_{22}Cl_2N_4O$: 52.18% C 6.42% H 16.23% N Found: 52.28% C 6.18% H 16.18% N

EXAMPLE 11

4-(2-Methyl-1-(1H)-imidazolyl)-1-phenyl-1-butanone O-(2-Aminoethyl)oxime Dihydrochloride A mixture of 4-(2-methyl-1-(1H)-imidazolyl)-1-phenyl-1-butanone (3.00 g), O-(2-aminoethyl)hydroxylamine dihydrochloride (2.35 g), 3 equivalents of pyridine, and absolute ethanol (75 ml) was heated under reflux, under nitrogen, with stirring, for four hrs. The solvent was evaporated, toluene was added and evaporated. The residue was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was purified by flash chromatography (180:19:1 dichloromethane/methanol/ammonium hydroxide). The appropriate fractions were collected and concentrated. The residue was dissolved in absolute ethanol and treated with ethereal hydrogen chloride. Diethyl ether was added. The precipitate was collected and recrystallized from absolute ethanol/ether to give 3.1 g (66%) of product, mp 153°–155° C.

Analysis: Calculated for $C_{16}H_{24}Cl_2N_4O$: 53.49% C 6.73% H 15.59% N Found: 53.39% C 6.79% H 15.47% N

EXAMPLE 12

1-(4-Chlorophenyl)-4-(1-(1H)-imidazolyl)-1-butanone O-(2-Aminoethyl)oxime Dihydrochloride A mixture of 1-(4-chlorophenyl)-4-(1-(1H)-imidazolyl)-1-butanone (2.20 g), O-(2-aminoethyl)hydroxylamine dihydrochloride (1.58 g), 3 equivalents of pyridine, and absolute ethanol (75 ml) was heated under reflux, under nitrogen, with stirring, for two hrs. The reaction mixture was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was taken up in toluene and evaporated. The residue was purified by flash chromatography (180:19:1 dichloromethane/methanol/ammonium hydroxide). The appropriate fractions were collected and concentrated. The residue was dissolved in absolute ethanol and treated with ethereal hydrogen chloride. Diethyl ether was added. The precipitate was collected and recrystallized twice from absolute ethanol/ether to give 1.3 g (39%) of product, mp 205°–207° C. (dec).

Analysis: Calculated for $C_{15}H_{21}Cl_3N_4O$: 47.45% C 5.57% H 14.75% N Found: 46.75% C 5.84% H 14.40% N

EXAMPLE 13

4-(1-(1H)-Imidazolyl)-1-(4-trifluoromethylphenyl)-1-butanone O-(2-Aminoethyl)oxime Dihydrochloride A mixture of 4-(1-(1H)-imidazolyl)-1-(4-trifluoromethylphenyl)-1-butanone (5.00 g), O-(2-aminoethyl)hydroxylamine dihydrochloride (3.17 g), 3 equivalents of pyridine, and absolute ethanol (75 ml) was heated under reflux, under nitrogen, with stirring, for two hrs. The reaction mixture was evaporated, toluene was added and evaporated. The residue was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was purified by flash chromatography (180:19:1 dichloromethane/methanol/ammonium hydroxide). The appropriate fractions were collected and concentrated. The residue was dissolved in absolute ethanol and treated with ethereal hydrogen chloride. Diethyl ether was added. The precipitate was collected and recrystallized twice from absolute ethanol/ether to give 3.1 g (42%) of product, mp 207°–208° C. (dec).

Analysis: Calculated for $C_{16}H_{21}Cl_2F_3N_4O$: 46.50% C 5.12% H 13.56% N Found: 46.29% C 4.97% H 13.67% N

EXAMPLE 14

4-(2-Methyl-1-(1H)-imidazolyl)-1-(4-trifluoromethylphenyl)-1-butanone O-(2-Aminoethyl)oxime Dihydrochloride A mixture of 4-(2-methyl-1-(1H)-imidazolyl)-1-(4-trifluoromethylphenyl)-1-butanone (2.65 g), O-(2-aminoethyl)hydroxylamine dihydrochloride (1.60 g), 3 equivalents of pyridine, and absolute ethanol (75 ml) was heated under reflux, under nitrogen, with stirring, for three hrs. The reaction mixture was diluted with 10% sodium hydroxide solution and ethyl acetate. The layers were separated. The aqueous phase was extracted with ethyl acetate. The organic layers were dried over anhydrous sodium sulfate, filtered, and the filtrate was evaporated. The residue was taken up in toluene and evaporated. The residue was purified by flash chromatography (180:19:1 dichloromethane/methanol/ammonium hydroxide). The appropriate fractions were collected and concentrated. The residue was dissolved in absolute ethanol and treated with ethereal hydrogen chloride. Diethyl ether was added. The precipitate was collected and recrystallized from absolute ethanol/ether to give 1.4 g (37%) of product, mp 181°–184° C. (dec).

Analysis: Calculated for $C_{17}H_{23}Cl_2F_3N_4O$: 47.79% C 5.43% H 13.11% N Found: 47.45% C 5.43% H 13.05% N

EXAMPLE 15

1-(4-Fluorophenyl)-4-(1-(1H)-imidazolyl)-1-butanone O-(2-Aminoethyl)oxime Dihydrochloride A mixture of 1-(4-fluorophenyl)-4-(1-(1H)-imidazolyl)-1-butanone (3.00 g), O-(2-aminoethyl)hydroxylamine dihydrochloride (2.31 g), 3 equivalents of pyridine, and absolute ethanol (75 ml) was heated under reflux, under nitrogen, with stirring, for four hrs. The reaction mixture was evaporated, toluene was added and evaporated. The residue was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was purified by flash chromatography (180:19:1 dichloromethane/methanol/ammonium hydroxide). The appropriate fractions were collected and concentrated. The residue was dissolved in absolute ethanol and treated with ethereal hydrogen chloride. Diethyl ether was added. The precipitate was collected and recrystallized from absolute ethanol to give 3.2 g (68%) of product, mp 237°–238° C. (dec).

Analysis: Calculated for $C_{15}H_{21}Cl_2FN_4O$: 49.60% C 5.83% H 15.42% N Found: 49.69% C 5.60% H 15.47% N

EXAMPLE 16

1-(4-Fluorophenyl)-4-(2-methyl-1-(1H)-imidazolyl)-1-butanone O-(2-Aminoethyl)oxime Dihydrochloride A mixture of 1-(4-fluorophenyl)-4-(2-methyl-1-(1H)-imidazolyl)-1-butanone (3.00 g), O-(2-aminoethyl)hydroxylamine dihydrochloride (2.18 g), 3 equivalents of pyridine, and absolute ethanol (75 ml) was heated under reflux, under nitrogen, with stirring, for three hrs. The reaction mixture was evaporated, toluene was added and evaporated. The residue was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was purified by flash chromatography (180:19:1 dichloromethane/methanol/ammonium hydroxide). The appropriate fractions were collected and concentrated. The residue was dissolved in absolute ethanol and treated with ethereal hydrogen chloride. Diethyl ether was added. The precipitate was collected and recrystallized from absolute ethanol/ether to give 3.2 g (70%) of product, mp 219°–221° C. (dec).

Analysis: Calculated for $C_{16}H_{23}Cl_2FN_4O$: 50.94% C 6.14% H 14.85% N Found: 51.01% C 6.22% H 14.78% N

EXAMPLE 17

1-(3,4-Dichlorophenyl)-4-(1-(1H)-imidazolyl)-1-butanone O-(2-Aminoethyl)oxime Dihydrochloride A mixture of 1-(3,4-dichlorophenyl)-4-(1-(1H)-imidazolyl)-1-butanone (2.29 g), O-(2-aminoethyl)hydroxylamine dihydrochloride (1.45 g), 3 equivalents of pyridine, and absolute ethanol (75 ml) was heated under reflux, under nitrogen, with stirring, for three hrs. The reaction mixture was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was taken up in toluene and evaporated. The residue was purified by flash chromatography (180:19:1 dichloromethane/methanol/ammonium hydroxide). The appropriate fractions were collected and evaporated. The residue was dissolved in absolute ethanol and treated with ethereal hydrogen chloride. Diethyl ether was added. The precipitate was collected and recrystallized twice from absolute ethanol/ether to give 1.1 g (33%) of product, mp 205°–208° C. (dec).

Analysis: Calculated for $C_{15}H_{20}Cl_4N_4O$: 43.50% C 4.87% H 13.53% N Found: 43.53% C 4.78% H 13.46% N

EXAMPLE 18

5-(1-(1H)-Imidazolyl)-1-(4-trifluoromethylphenyl)-1-pentanone O-(2-Aminoethyl)oxime Dihydrochloride A mixture of 5-(1-(1H)-imidazolyl)-1-(4-trifluoromethylphenyl)-1-pentanone (11.5 g), O-(2-aminoethyl)hydroxylamine dihydrochloride (5.78 g), 3 equivalents of pyridine, and absolute ethanol (75 ml) was heated under reflux, under nitrogen, with stirring, for three hrs. The reaction mixture was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was taken up in toluene and evaporated. The residue was purified by flash chromatography (180:19:1 dichloromethane/methanol/ammonium hydroxide). The appropriate fractions were collected and evaporated. The residue was dissolved in absolute ethanol and treated with ethereal hydrogen chloride. Diethyl ether was added. The precipitate was collected and recrystallized twice from absolute ethanol/ether to give 3.3 g (20%) of product, mp 115°–120° C. (dec).

Analysis: Calculated for $C_{17}H_{23}Cl_2F_3N_4O$: 47.79% C 5.43% H 13.11% N Found: 46.99% C 5.39% H 12.83% N

EXAMPLE 19

4-[4-(4-Fluorobenzoyl)-1-piperidinyl]-1-phenyl-1-butanone O-(2-Aminoethyl)oxime Dihydrochloride A mixture of 4-[4-(4-fluorobenzoyl)-1-piperdinyl]-1-phenyl-1-butanone (5.00 g), O-(2-aminoethyl)hydroxylamine dihydrochloride (2.21 g), 3 equivalents of pyridine, and absolute ethanol (75 ml) was stirred at 60° C., overnight, under nitrogen. The reaction mixture was evaporated, toluene was added and evaporated. The reaction mixture was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was purified by flash chromatography (180:19:1 dichloromethane/methanol/ammonium hydroxide). The appropriate fractions were collected and evaporated. The residue was dissolved in absolute ethanol and treated with ethereal hydrogen chloride. Diethyl ether was added. The precipitate was collected and recrystallized twice from absolute ethanol/ether to give 2.3 g (34%) of product, mp 110°–115° C. (dec).

Analysis: Calculated for $C_{24}H_{32}Cl_2FN_3O_2$: 59.50% C 6.66% H 8.67% N Found: 59.18% C 6.96% H 8.69% N

EXAMPLE 20

1-{1-[4-(2-Aminoethoxyimino)-4-(4-chlorophenyl)butyl]-4-piperidinyl}-1,3-dihydro-2-benzimidazolone Dihydrochloride A mixture of 1-{1-[4-oxo-4-(4-chlorophenyl)butyl]-4-piperidinyl}-1,3-dihydro-2-benzimidazolone (3.00 g), O-(2- aminoethyl)hydroxylamine dihydrochloride (1.35 g), 3 equivalents of pyridine, and absolute ethanol (75 ml) was heated under reflux, under nitrogen, with stirring, for three hrs. The reaction mixture was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was taken up in toluene and evaporated. The residue was purified by flash chromatography (180:19:1 dichloromethane/methanol/ammonium hydroxide). The appropriate fractions were collected and evaporated. The residue was dissolved in absolute ethanol and treated with ethereal hydrogen chloride. The solvent was evaporated, and the residue was taken up in hot 2-propanol and chilled. The precipitate was collected and recrystallized twice from absolute ethanol/ether to give 2.1 g (53%) of product, mp 140°–145° C. (dec).

Analysis: Calculated for $C_{24}H_{32}Cl_3N_5O_2$: 54.50% C 6.10% H 13.24% N Found: 53.86% C 6.44% H 12.93% N

EXAMPLE 21

1-{1-[4-(2-Aminoethoxyimino)-4-phenylbutyl]-4-piperidinyl}-1,3-dihydro-2-benzimidazolone Dihydrochloride A mixture of 1-[1-(4-oxo-4-phenylbutyl)-4-piperidinyl]-1,3-dihydro-2-benzimidazolone (3.85 g), O-(2-aminoethyl)hydroxylamine dihydrochloride (1.89 g), 3 equivalents of pyridine, and absolute ethanol (75 ml) was heated under reflux, under nitrogen, with stirring, for three hrs. The reaction mixture was partitioned between 10% sodium hydroxide solution and ethyl acetate. The layers were separated and the aqueous phase extracted with ethyl acetate. The combined organic extracts were dried over anhydrous sodium sulfate, filtered, and the filtrate was evaporated. The residue was taken up in toluene and evaporated. The residue was purified by flash chromatography (180:19:1 dichloromethane/methanol/ammonium hydroxide). The appropriate fractions were collected and evaporated. The residue was dissolved in absolute ethanol and treated with ethereal hydrogen chloride. The solvent was evaporated and the residue was taken up in hot 2-propanol and chilled. The precipitate was collected and recrystallized from 2-propanol and then twice from ethanol/ether to give 1.5 g (29%) of product, mp 175°–180° C. (dec).

Analysis: Calculated for $C_{24}H_{33}Cl_2N_5O_2$: 58.30% C 6.73% H 14.16% N Found: 57.73% C 6.93% H 13.83% N

EXAMPLE 22

Cyclopropyl-[4-(2-phenyl-1-imidazolyl)phenyl]methanone O-(2-Aminoethyl)oxime Dihydrochloride A mixture of cyclopropyl-[4-(2-phenyl-1-imidazolyl)phenyl]methanone (2.6 g), aminoethylhydroxylamine dihydrochloride (1.95 g), and 3 equivalents of pyridine, in absolute ethanol (30 ml) was heated under reflux, under nitrogen, with stirring, overnight. The reaction mixture was evaporated, the residue was taken up in ethyl acetate and washed with a 10% sodium hydroxide solution. The organic extracts were evaporated and the residue purified by high performance liquid chromatography (silica gel, 185:14:1 dichloromethane/methanol/ammonium hydroxide). The appropriate fractions were collected and concentrated. The residue was taken up in ethanol and treated with ethereal hydrogen chloride. The mixture was evaporated. The residue was recrystallized from ethanol/ether to give 3.06 g (80.9%) of product, mp >220° C. (dec).

Analysis: Calculated for $C_{21}H_{24}Cl_2N_4O_2$: 60.15% C 5.77% H 13.36% N Found: 60.18% C 6.06% H 13.20% N

EXAMPLE 23

Cyclopropyl-[4-(2-phenyl-1-imidazolyl)phenyl]methanone

A solution of 4-chloro-4'-fluorobutyrophenone (15.0 g) and 2-phenylimidazole (100 mL) in dry dimethylformamide was heated, under nitrogen, at 150° C., with stirring, overnight. The reaction mixture was cooled, diluted with water and extracted with ethyl acetate. The organic extracts were evaporated and the residue was purified by high performance liquid chromatography (silica gel, dichloromethane to 1% methanol/dichloromethane). The appropriate fractions were collected and concentrated. The residue was recrystallized from ethanol to give 4.3 g (19.9%) of product, mp 155°–157° C.

Analysis: Calculated for $C_{19}H_{16}N_2O$: 79.14% C 5.59% H 9.71% N Found: 79.03% C 5.49% H 9.72% N

REACTION SCHEME

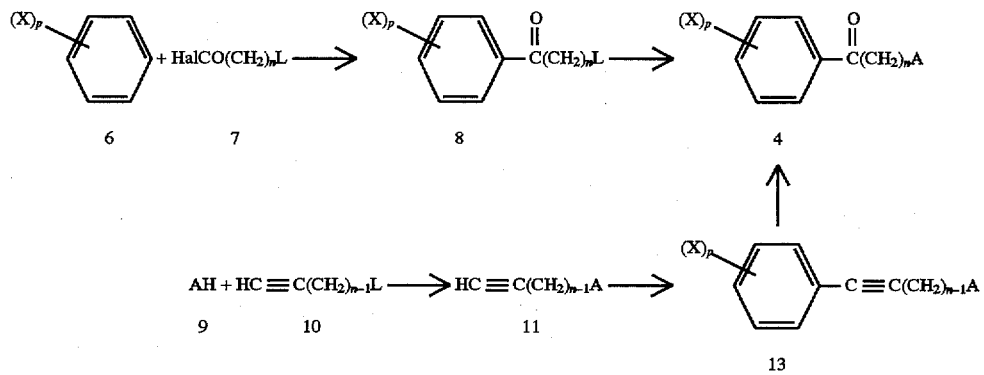

-continued
REACTION SCHEME

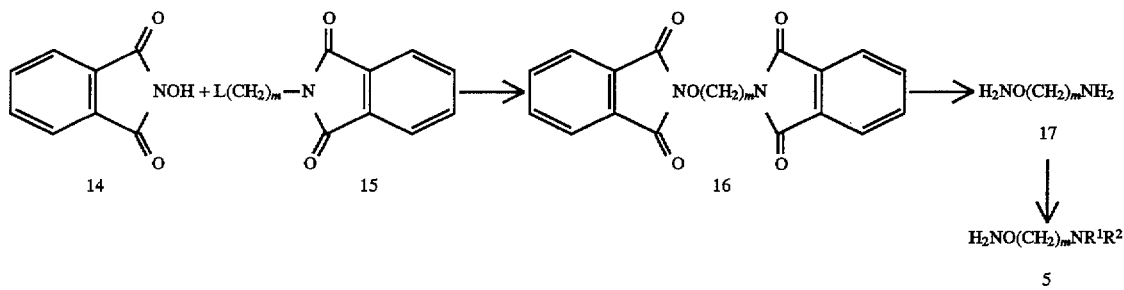

We claim:

1. A compound of the formula

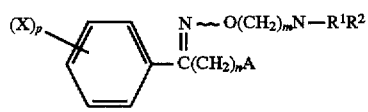

wherein:

a. X is hydrogen, loweralkyl, loweralkoxy, halogen, trifluoromethyl, or a group of the formula

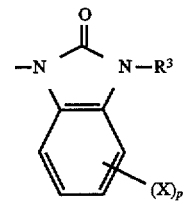

wherein Y is hydrogen or loweralkyl, and p is 1 or 2;

b. A is a group of the formula

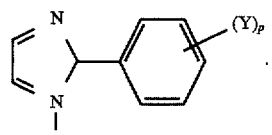

wherein r is 1, and B is a group of the formula

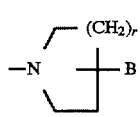

wherein X and p are as above or B is a group of the formula

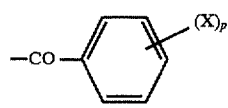

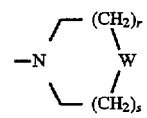

wherein $R^3$ or is hydrogen or loweralkyl and X and p are as above;

c. $R^1$ and $R^2$ are independently hydrogen or loweralkyl or $R^1$ and $R^2$ taken together with the nitrogen atom to which they are attached form a group of the formula wherein W is $CH_2$, O or S, r is 1, 2, or 3, and s is 1,2, or 3;

d. m and n are 2 to 6, inclusive, the geometric and optical isomers thereof; or the pharmaceutically acceptable salts thereof.

2. A method of treating depression in mammals comprising administering to a mammal in need of depression treatment, a depression treating effective amount of a compound according to claim 1.

3. A method of treating obsessive compulsive disorders in mammals comprising administering to a mammal in need of obsessive compulsive disorder treatment, an obsessive compulsive disorder treating effective amount of a compound according to claim 1.

4. A depression treating composition comprising an inert adjuvant and as the active ingredient an amount effective in treating depression of a compound according to claim 1.

5. An obsessive compulsive disorder treating composition comprising an inert adjuvant and as the active ingredient an amount effective in treating obsessive compulsive disorders of a compound according to claim 1.

* * * * *